United States Patent [19]

Daniels et al.

[11] 4,391,992
[45] Jul. 5, 1983

[54] N-DENITRATION OF N,2,6-TRINITROANILINES WITH PHASE TRANSFER CATALYSTS

[75] Inventors: William A. Daniels, Belle Mead; Rainer K. Zawadzki, Hopewell, both of N.J.

[73] Assignee: American Cyanamid Company, Stamford, Conn.

[21] Appl. No.: 195,264

[22] Filed: Oct. 8, 1980

Related U.S. Application Data

[63] Continuation-in-part of Ser. No. 69,451, Aug. 24, 1979, abandoned.

[51] Int. Cl.$^3$ .................. C07C 85/11; C07C 76/02; C07C 85/24; C07C 85/26; C07C 87/60; C07C 87/62; C07C 79/10; C07C 79/12
[52] U.S. Cl. .................................. 564/441; 568/933; 568/932; 564/107
[58] Field of Search ............... 568/932, 933, 936, 939; 564/441, 112, 107

[56] References Cited

U.S. PATENT DOCUMENTS

| | | | |
|---|---|---|---|
| 3,332,769 | 7/1967 | Joper | 564/441 |
| 3,403,180 | 9/1968 | Joper | 564/441 |
| 3,764,624 | 10/1973 | Strong et al. | 564/441 |
| 3,920,742 | 11/1975 | Lutz et al. | 564/441 |
| 3,991,116 | 11/1976 | Damiano | 568/933 |
| 3,992,432 | 11/1976 | Napier et al. | 260/465.1 |
| 4,120,905 | 10/1978 | Cannon et al. | 568/933 |
| 4,134,917 | 1/1979 | Ross et al. | 564/441 |
| 4,180,679 | 12/1979 | Kapoor | 564/441 |
| 4,185,035 | 1/1980 | Eizember et al. | 568/933 |

FOREIGN PATENT DOCUMENTS 19158  5/1980  European Pat. Off. ............ 564/441

OTHER PUBLICATIONS

White, W. N., et al., JACS, vol. 86, pp. 1517–1520, (Apr. 20, 1964).

Primary Examiner—Teddy S. Gron
Attorney, Agent, or Firm—H. G. Jackson

[57] ABSTRACT

A method for the N-denitration of secondary N,2,6-trinitroanilines with phase transfer catalysts.

7 Claims, No Drawings

N-DENITRATION OF N,2,6-TRINITROANILINES WITH PHASE TRANSFER CATALYSTS

The invention provides a procedure for the rapid elimination of a nitro group attached to the amino function of a secondary trinitroaniline of formula (I) obtained during the preparation of herbicidal dinitroaniline compounds of formula (II); both schematically illustrated below:

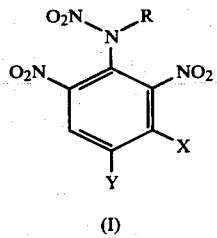 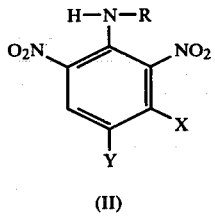

(I)    (II)

wherein R is $C_1$–$C_6$ alkyl (straight chain, or preferably branched, especially secondary alkyl), $C_4$–$C_6$ cycloalkyl, $C_1$–$C_4$ monohaloalkyl or $C_1$–$C_4$ alkoxy($C_2$–$C_4$)alkyl; Y is $C_1$–$C_4$ alkyl, halogen or $CF_3$; X is hydrogen, halogen, $C_1$–$C_4$ alkyl, $C_1$–$C_4$ alkoxy, $C_1$–$C_4$ monohaloalkyl or $C_1$–$C_4$ alkoxy($C_1$–$C_4$)alkyl; wherein the above denitration procedure comprises: reacting the formula (I) compound with a phase transfer catalyst in the presence of an aqueous solution of a strong base, as hereinbelow discussed and described in detail.

Among the compounds represented by formula (I) and (II), a preferred group of compounds are those wherein R is $C_3$–$C_6$ alkyl (straight chain, or preferably a secondary alkyl); Y is $C_1$–$C_3$ alkyl or $CF_3$; X is hydrogen, $CH_3$ or $CH_3OCH_2$.

The most preferred compounds of formulae (I) and (II) are those wherein R is 1-ethylpropyl; Y is methyl or isopropyl; X is methyl or methoxymethyl.

The compounds of formula (I) are obtained as the unwanted by-products of nitration reactions designed to prepare the herbicidal dinitroanilines of formula (II). It should be noted here that, in the course of the above-referred-to nitration reactions, N-nitroso-dinitroanilines of formula (IV) are formed too. The above-referred-to nitration reaction is hereinbelow schematically illustrated:

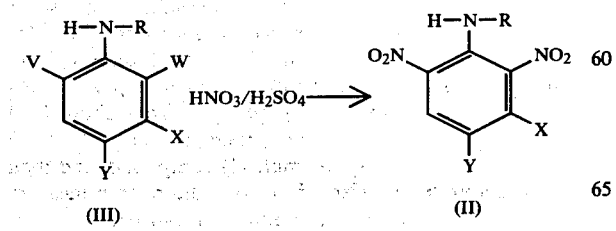

(III)    (II)

The unwanted by-products of this reaction are:

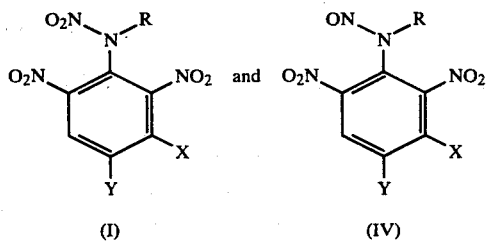

(I)    (IV)

wherein in the above reaction scheme, R, X and Y are as hereinabove defined; and V and W are both hydrogen, or if only one of them is hydrogen, then the other must be nitro.

The compounds of formula (III) may be nitrated conveniently by dissolving same in an inert water-immiscible solvent, such as ethylene dichloride, chloroform, carbon tetrachloride, monochlorobenzene, and the like, and preferably ethylene dichloride, and monochlorobenzene, and then the solution is added to a stirred nitration mixture consisting of nitric acid and sulfuric acid at a rate designed to control the ensuing exothermic reaction within the desired temperature limits. On completion of the reaction, the organic phase is separated. This phase contains in addition to the desired herbicides of formula (II) the N-nitro- (I) and N-nitroso- (IV) dinitroaniline impurities. Obviously, formation of compounds of formulae (I) and (IV) results in lower yields of the desired formula (II) herbicidal dinitroanilines. Advantageously, the formula (IV) impurities may be reconverted by chemical means to the desired formula (II) products, and, consequently, the yield of these herbicides (II) can be improved. More important is, however, the fact that these unwanted impurities, especially of formula (IV), may be either completely eliminated from, or at least lowered to acceptable levels in the products (II).

Thus, it is known that formula (IV) nitroso compounds may be denitrosated with sulfamic acid to the corresponding formula (II) pesticides either by treating the nitration mixture or the isolated organic phase with sulfamic acid. This denitrosation reaction may be carried out, however, more advantageously by the method of U.S. Pat. No. 4,134,917, issued Jan. 16, 1979 (Assignee: American Cyanamid Company), incorporated herein by way of reference and illustrated in Example 5.

It should be noted here, that the thermal decomposition of formula (I) N-nitroanilines may also result in the formation of formula (IV) N-nitrosoanilines, as illustrated below:

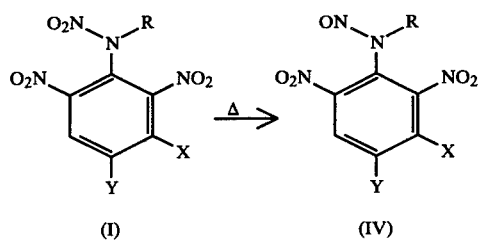

(I)    (IV)

wherein R, X and Y are also hereinabove defined. The significance of this reaction is in that after the N-nitroso compounds of formula (IV) have been removed from the above-discussed nitration mixture of the product isolated therefrom, any formula (I) N-nitroaniline present in either the organic phase of the nitration mixture or in the product isolated therefrom, may thermally decompose and regenerate this undesirable contaminant (IV).

The N-denitration of secondary N-nitroamines is known to take place when these compounds are heated in aqueous potassium hydroxide. We find, however, that this denitration does not proceed at an acceptable rate with the N,2,6-trinitroanilines of formula (I) of the present invention.

Advantageously, by the novel method of the present invention, N-nitroanilines of formula (I) may be removed from the above-said nitration mixture or the products isolated therefrom with bases in the presence of phase transfer catalysts.

Thus, the separated organic phase of a nitration mixture comprising: a solution of compounds of formulae (I), (II) and (IV) in a solvent, such as ethylene dichloride, chloroform, carbon tetrachloride, monochlorobenzene, and the like, preferably ethylene dichloride, or chlorobenzene, is first denitrosated by the method of U.S. Pat. No. 4,134,917 and is then mixed with a phase transfer catalyst selected from ternary and quaternary salts of formula (V)

$$R_n^1-Q^+\cdot Z^- \quad (V)$$

wherein n is an integer of 2,3 or 4; and thus $R^1$ represents two, three or 4 substituent in formula V compound, wherein each of these may be the same or different and is selected from $C_1$—$C_{16}$ alkyl (straight chain or branched), $C_3$-$C_7$ cycloalkyl optionally substituted with $C_1$-$C_3$ alkyl, benzyl, substituted benzyl, phenyl or substituted phenyl wherein the substituent is halogen, $C_1$-$C_3$ alkyl, $C_1$-$C_3$ alkoxy and the like; Q is N,P, As or S; anion Z is Cl, Br, I, H SO$_4$, CH$_3$SO$_4$, H$_2$PO$_3$ or H$_2$PO$_4$. Other phase transfer catalysts may be selected from macrocylic and macrobicyclic ethers such as 18 Crown 6 and [2,2,2] cryptate

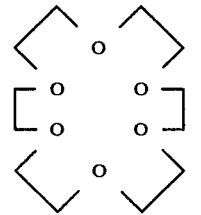

18 Crown 6

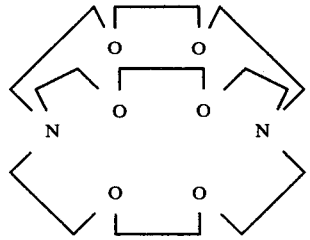

[2,2,2] cryptate;

polyethers such as polyethylene glycols of formula HO—(CH$_2$CH$_2$O—)$_m$ CH$_2$CH$_2$OH wherein m is an integer of 40 to 50; phosphate esters such as the mono- and diesters of orthophosphonic acid made from certain ethylene oxide adducts or from $C_4$-$C_7$ cycloalkyl alcohols wherein the latter may be substituted, if so desired; as illustrated below:

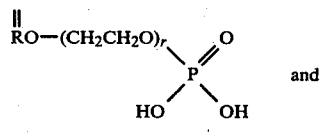

and

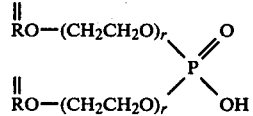

wherein R'' is $C_1$-$C_3$ alkyl, r is an integer of from 8 to 25; or

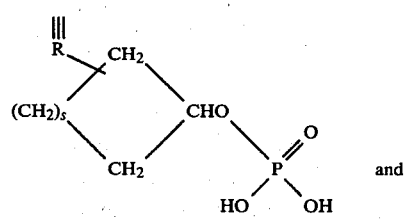

and

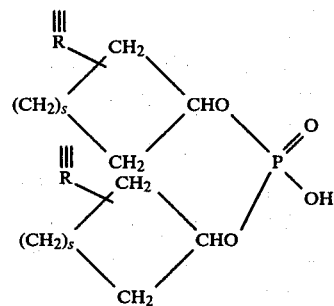

wherein R is hydrogen or $C_1$-$C_4$ alkyl; s is an integer of from 1 to 4;

sulfate ester analogs of the above may also be used; N-alkyl phosphoramides, methylene bridged phosphorus and sulfur oxides; quaternized heterocyclic compounds such as alkylpyridinium salts or various substituted pyrazolium salts.

Among the phase transfer catalysts discussed and described above the following are of particular interest: tetra-n-butylammonium salts, tricapryl methylammonium salts, benzyl trimethylammonium salts, tetra-n-butylphosphonium salts, hexadecylpyridinium salts, 1,2-dimethyl-3,5-diphenylpyrazolium salts, 18 Crown 6 ether, and the like, and wherein said salts are the chlorides, bromides, hydrogen sulfate, methyl sulfates, dihydrogen phosphates and the like. The above phase transfer catalysts are used in amounts of from about 0.15 mole to about 4.0 moles, and preferably 0.8 mole to 3.0 moles per mole of said formula (I) compound, and then an aqueous base, selected from sodium or potassium hydroxide or carbonate, ammonium hydroxide or carbonate, is added in amounts sufficient to maintain a pH of 7 or more throughout the reaction. The resulting two-phase mixture is rapidly agitated at reflux by suitable means for a period of from 5 to 120 minutes, or until the reaction is essentially complete, and the amount of formula (I) compound originally present in said mixture is reduced to zero or to an acceptable level. Next, the two phases are separated, and the described herbicidal 2,6-dinitroaniline of formula (II) is recovered from the organic phase.

Thus, for instance, 200 g of the organic phase of a nitration reaction, from which the N-(1-ethylpropyl)-2,6-dinitro-N-nitroso-3,4-xylidine has been removed by the denitrosation method of U.S. Pat. No. 4,134,917; and now comprises: a solution of 120 g of N-(1-ethylpropyl)-2,6-dinitro-3,4-xylidine and 0.3 g of N-(1-ethylpropyl)-N,2,6-trinitro-3,4-xylidine in 80 g of ethylene dichloride is mixed with 20 g of 10% sodium hydroxide solution and 0.36 g of benzyl triethylammonium chloride. The resulting two-phase reaction mixture is agitated rapidly by suitable means and heated at reflux for one hour, diluted with water, the organic phase separated, and the product isolated by standard laboratory procedures. The isolated product is found to be free of the corresponding formula (I) nitramine.

Substitution of tetra-n-butylphosphonium chloride, tri-(4-hydroxyphenyl)sulfonium chloride, hexadecylpyridinium chloride, 1,2-dimethyl-3,5-diphenylpyrazolium methylsulfate, 18 Crown 6 ether of formula

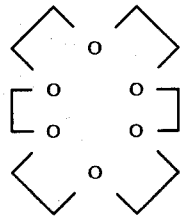

[2,2,2] cryptate of formula

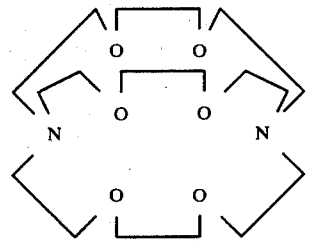

for benzyl triethylammonium chloride in the above procedure results in formula (II) product, essentially free of the undesired nitramine of formula (I).

EXAMPLE 1

Denitration of N-(1-Ethylpropyl)-N,2,6-trinitro-3,4-xylidine

A solution of N-(1-ethylpropyl)-2,6-dinitro-3,4-xylidine (120 g) and N-(1-ethylpropyl)-N,2,6-trinitro-3,4-xylidine (0.3 g) in ethylene dichloride (80 g) is mixed with 10% sodium hydroxide solution (20 g) and benzyl triethylammonium chloride (0.36 g). The reaction mixture is stirred and heated at reflux for one hour. Water (100 g) is added, the phases are separated, and the aqueous phase washed with ethylene dichloride (2×50 ml). The organic phase and washings are combined, and the solvent evaporated under vacuum to afford 120.59 g solid. By analysis, this solid contains 97.6% by weight of N-(1-ethylpropyl)-2,6-dinitro-3,4-xylidine, 600 ppm of N-(1-ethylpropyl)-N,2,6-trinitro-3,4-xylidine and <60 ppm of N-(1-ethylpropyl)-2,6-dinitro-N-nitroso-3,4-xylidine.

EXAMPLE 2

Denitration of N-(1-Ethylpropyl)-N,2,6-trinitro-3,4-xylidine

To the isolated phase of a nitration mixture comprising: a solution of N-(1-ethylpropyl)-2,6-dinitro-3,4-xylidine (a), N-(1-ethylpropyl)-N,2,6-trinitro-3,4-xylidine (b), and N-(1-ethylpropyl)-2,6-dinitro-N-nitroso-3,4-xylidine (c), in ethylene dichloride (weight of solution: 22.2 kg), is added a 15% aqueous sodium hydroxide solution (1.25 kg) and benzyl triethylammonium chloride (0.136 kg), and the mixture is stirred and heated at reflux for 2 hours. Next, water (11.32 kg) is added, the mixture stirred, and the two phases are then separated. A sample of the organic phase is taken and evaporated to dryness under vacuum, and the solid residue analyzed. The data obtained are compared to those obtained by analyzing the above-referred-to organic phase of a nitration mixture, and are shown below:

| Compound | Analysis | |
| --- | --- | --- |
| | Start | End |
| a | 38.8% | 39.8% |
| b | 7368 ppm | <3 ppm |
| c | 14.4% | 11.9% |

It can be clearly seen from the above data, that the novel process of the present invention effectively removes the unwanted N-nitro compound (b) from the crude reaction mixture.

EXAMPLE 3

Denitration of N-(1-Ethylpropyl)-N,2,6-trinitro-3,4-xylidine

A solution of N-(1-ethylpropyl)-2,6-dinitro-3,4-xylidine (a), N-(1-ethylpropyl)-N,2,6-trinitro-3,4-xylidine (b), and N-(1-ethylpropyl)-2,6-dinitro-N-nitroso-3,4-xylidine (c) in ethylene dichloride (weight of solution: 200 g), is mixed with a 10% aqueous solution of potassium hydroxide (20 g) and benzyl triethylammonium chloride (0.3164 g). The reaction mixture is stirred, heated to reflux in about 20 minutes and refluxed for one hour. Hot water (100 g at 82° C.) is added, the mixture stirred for 5 minutes, and then the phases are separated. The thus-obtained organic phase is analyzed, and the data obtained are compared to those obtained by analyzing the solution prior to the denitration of same with the above base and phase transfer catalyst.

| Compound | Analysis | |
| --- | --- | --- |
| | Start | End |
| a | 58.6% | not determined |
| b | 1065 ppm | <2 ppm |
| c | 9 ppm | 9 ppm |

EXAMPLE 4

Denitration of N-(1-Ethylpropyl)-N,2,6-trinitro-3,4-xylidine

The same experiment of Example 3 is repeated twice, using samples of the same solution, except that no benzyl triethylammonium chloride is added to the reaction mixtures. On completion of the reactions, the mixtures are worked up as in Example 3, and analyzed for N-(1-ethylpropyl)-2,6-dinitro-3,4-xylidine (a), N-(1-ethylpropyl)-N,2,6-trinitro-3,4-xylidine (b), and N-(1-ethylpropyl)-2,6-dinitro-N-nitroso-3,4-xylidine (c). The thus-obtained analytical data are compared to the values obtained by analyzing the starting material used in these runs (the starting material is the same as the one used in said Example 3).

| Sample | Analysis (a) % | (b) ppm | (c) ppm |
|---|---|---|---|
| Starting Material | 58.6 | 1065 | 9 |
| Run I | not determined | 641 | 12 |
| Run II | 61.0 | 646 | 10 |

EXAMPLE 5

Denitrosation of N-(1-Ethylpropyl)-2,6-dinitro-N-nitroso-3,4-xylidine with Diethyl Ketone A glass pressure reactor is charged with an ethylene dichloride solution (96.0 g) of N-(1-ethylpropyl)-2,6-dinitro-3,4-xylidine (38.2% by weight=36.7 g) and N-(1-ethylpropyl)-2,6-dinitro-N-nitroso-3,4-xylidine (13.4% by weight=12.9 g), concentrated hydrochloric acid (14.7 g) and diethyl ketone (2.5 g), and the reactor is then sealed. The reaction mixture is heated to 80°–85° C. and stirred for 4 hours while the temperature is maintained at 80°–88° C. The pressure increases within the vessel to a maximum of 1.68 kg/cm² and then slowly decreases to 1.26 kg/cm² in the course of the reaction. On completion of the reaction, the reactor is cooled down, vented, the pH of the reaction mixture adjusted to 10 with 10% sodium hydroxide and filtered. The filtercake is washed several times with ethylene dichloride, the organic layer separated, and the solvent removed under vacuum to afford 51.4 g of solid containing (by analysis) 93.3% by weight of N-(1-ethylpropyl)-2,6-dinitro-3,4-xylidine (47.9 g) and <0.01% by weight of N-(1-ethylpropyl)-2,6-dinitro-N-nitroso-3,4-xylidine (0.51 g).

EXAMPLE 6

Preparation of N-(1-Ethylpropyl)-2,6-dinitro-3,4-xylidine

A nitration mixture is prepared by adding 70.5% nitric acid (145.2 g; 1.625 mol) and 94.5% sulfuric acid (116.2 g; 1.12 mol) to water (58.8 g). To the above-mixed acid, a solution of 94.6% pure N-(1-ethylpropyl)-3,4-xylidine (101.0 g; 0.5 mol) in ethylene dichloride (143.5 ml) is added over a period of 2 hours at 35° C. The reaction mixture is stirred at 35° C. for one hour, and the aqueous phase is then separated. The organic phase is washed successively with 5% sodium hydroxide (300 ml) and water (300 ml) and is then dried over magnesium sulfate. The organic solution is then concentrated under vacuum at 70° C. to yield 141.5 g of a solid containing 117.0 g (72.6%) of title product.

By the above procedure, but substituting monochlorobenzene for ethylene dichloride, the title product is obtained in similar yields and purity.

EXAMPLE 7

Denitration of N-(1-Ethylpropyl)-N,2,6-trinitro-3,4-xylidine

The separated organic phase of a nitration mixture obtained by the procedure of Example 6, wherein the solvent of said organic phase is monochlorobenzene, is first denitrosated by the procedure of Example 5, and is then denitrated by the procedure of Example 2. The organic phase is analyzed before and after the denitration reaction. The data obtained are shown below:

| Compound | Analysis Start | End |
|---|---|---|
| b | 1000 ppm | 65 ppm* |
|   |          | <2 ppm** |
| c | <20 ppm | 6 ppm* |
|   |          | 7 ppm** |

*In 30 minutes at 70° C.
**After an additional 30 minutes at 87° C.

A second experiment, performed as above, yields the following data:

| Compound | Analysis Start | End |
|---|---|---|
| b | 2750 ppm | <2 ppm* |
|   |          | <2 ppm** |
| c | 42 ppm | 14 ppm* |
|   |        | 14 ppm** |

*In 30 minutes at 70° C.
**After an additional 30 minutes at 87° C.

In the above Examples, b and c have the same definition as in Example 2.

EXAMPLE 8

Denitration of N-(1-ethylpropyl)-N,2,6-trinitro-3,4-xylidine

A number of reactions are run to compare the effect of benzyl triethylammonium chloride (BTEAC) and of tetra-n-butylphosphonium chloride (TBPC) on the N-denitration of the title product, respectively.

Procedure

Pure samples of N-(1-ethylpropyl)-2,6-dinitro-3,4-xylidine are blended with 4000, 2000, 1000 and 500 ppm of N-(1-ethylpropyl)-N,2,6-trinitro-3,4-xylidine.

A sample (6.0 g) of each blend is mixed with chlorobenzene (4.0 g) and with 1.0 g of a solution of BTEAC (0.04966 g) in 15% sodium hydroxide (100 g), or with 1.0 g of a solution of TBPC (60% pure; 0.10864 g) in 15% sodium hydroxide (100 g), respectively.

The mixtures are heated at 87±2° C. for one hour, water (5.0 g) is then added. The organic phase is separated and the amount of N-(1-ethylpropyl)-N,2,6-trinitro-3,4-xylidine present is determined.

The data obtained are shown in Table I below.

TABLE I

The effect of various phase transfer catalyst on the denitration of N—(1-ethylpropyl)-N,2,6-trinitro-3,4-xylidine

| N—(1-ethylpropyl)-N,2,6-trinitro-3,4-xylidine present (in ppm) | | |
|---|---|---|
| at the start | at the end, with phase transfer catalyst | |
|  | BTEAC | TBPC |
| 4000 | 1320 | 1400 |
| 2000 | 650 | 670 |
| 1000 | 305 | 270 |

TABLE I-continued

The effect of various phase transfer catalyst on the denitration of
N—(1-ethylpropyl)-N,2,6-trinitro-3,4-xylidine N—(1-ethylpropyl)-N,2,6-trinitro-3,4-xylidine
present (in ppm)

| at the start | at the end, with phase transfer catalyst | |
|---|---|---|
|  | BTEAC | TBPC |
| 500 | 170 | 100 |

EXAMPLE 9

Evaluation of various phase transfer catalyst for the denitration of N-(1-ethylpropyl)-N,2,6-trinitro-3,4-xylidine Procedure To the isolated organic phase of a nitration mixture comprising: a solution of N-(1-ethylpropyl)-2,6-dinitro-3,4-xylidine (a), N-(1-ethylpropyl)-N,2,6-trinitro-3,4-xylidine (b) and N-(1-ethylpropyl)-2,6-dinitro-N-nitroso-3,4-xylidine (c), in ethylene dichloride or chlorobenzene (250 g), sodium hydroxide solution (15% w/w; 50 g) and a phase transfer catalyst are added.

The mixture is stirred and heated at 90° C. for 0.5 hours. Water (103.5 g) is then added, the organic phase separated and the amount of undesired by-products (b and c) determined. The data obtained are summarized in Table II below together with other pertinent data relating to these experiments.

TABLE II

Evaluation of various phase transfer catalysts for the denitration of N—(1-ethylpropyl)-N,2,6-trinitro-3,4-xylidine

| Experiment | Phase Transfer Catalyst (PTC) | PTC used as % by wt of organic phase | b ppm | c ppm |
|---|---|---|---|---|
| Starting Material | — | — | 680 | 35 |
| 1 | Benzyltriethylammonium chloride | 0.56 | <15 | 35 |
| 2 | Trioctyl methylammonium chloride | 0.39 | <14 | 130 |
| 3 | 1,2-dimethyl-3,5-diphenyl-pyrazolium methylsulfate | 0.80 | 7 | 25 |
| 4 | Hexadecylpyridinium chloride | 0.10 | 580 | 36 |
| 5 | tetra-n-butylammonium hydrogen sulfate | 0.34 | 47 | 135 |
| 6 | tetra-n-butyl phosphonium chloride | 0.14 | <2 | 36 |
| 7 | triphenylsulfonium chloride | 0.48 | 310 | 36 |
| 8 | blemd of amionic and nonionic emulsifiers | 5.9 | <70 | 37 |

We claim:

1. A process for the N-denitration of a compound of formula:

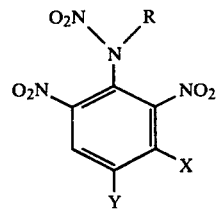

wherein R is $C_1$–$C_6$ alkyl, $C_4$–$C_6$ cycloalkyl, $C_1$–$C_4$ monohaloalkyl or $C_1$–$C_4$ alkoxy($C_2$–$C_4$)alkyl; Y is $C_1$–$C_4$ alkyl, halogen or $CF_3$; X is hydrogen, halogen, $C_1$–$C_4$ alkyl, $C_1$–$C_4$ alkoxy, $C_1$–$C_4$ monohaloalkyl or $C_1$–$C_4$ alkoxy($C_1$–$C_4$) alkyl; comprising: reacting the compound with 0.15 to 4.0 molar amount of a phase transfer catalyst, wherein said catalyst is the moiety $R_n^1$—$Q^+.Z^-$, n is an integer of 2,3 or 4; wherein each $R^1$ may be the same or different and is selected from $C_1$–$C_{16}$ alkyl, $C_3$–$C_7$ cycloalkyl optionally substituted with $C_1$–$C_3$ alkyl, benzyl, substituted benzyl, phenyl, substituted phenyl and the substitutent is HO, halogen, $C_1$–$C_3$ alkyl, $C_1$–$C_3$ alkoxy, Q is N,P,As or S, Z is Cl, Br, I, $HSO_4$, $CH_3SO_4$, $H_2PO_3$ or $H_2PO_4$, or said catalyst is macrocyclic ethers, macrobicyclic ethers, polyethylene glycols of formula HO—($CH_2CH_2O$—)$_m$—$CH_2CH_2OH$ and m is an integer of 40 to 50, mono and diesters of orthophosphonic acid with ethylene oxide adducts, alkylpyridinium salts or substituted pyrazolium salts; in the presence of a water-immiscible solvent of ethylene dichloride, chloroform, monochlorobenzene or carbon tetrachloride; and in the presence of an aqueous solution of an alkali metal hydroxide or carbonate or ammonium hydroxide in amounts sufficient to maintain at least pH 7 throughout the reaction; and wherein the thus-obtained two-phase reaction mixture is agitated at reflux until the reaction is essentially complete.

2. A process according to claim 1, wherein said phase transfer catalyst is tricapryl methylammonium salt, benzyl trimethylammonium salt, benzyl triethylammonium salt; tetra-n-butylphosphonium salt, alkylpyridinium salt or substituted pyrazolium salt.

3. A process according to claim 1 wherein R is $C_3$–$C_6$ alkyl, Y is $C_1$–$C_3$ alkyl or $CF_3$, X is hydrogen, $CH_3$ or $CH_3OCH_2$—; said phase transfer catalyst is benzyl trimethylammonium salt, benzyl triethylammonium salt or tetra-n-butylphosphonium salt.

4. A process according to claim 2 wherein the compound is N-(1-ethylpropyl)-N,2,6-trinitro-3,4-xylidine.

5. A process according to claim 3 wherein the phase transfer catalyst is benzyl triethylammonium chloride, the solvent is ethylene dichloride, and the base is sodium hydroxide.

6. A process according to claim 4 wherein the phase transfer catalyst used in 0.8 to 3.0 molar amounts.

7. A process according to claim 2 wherein the solvent is monochlorobenzene.

* * * * *